United States Patent
Levine et al.

(10) Patent No.: US 10,293,010 B2
(45) Date of Patent: May 21, 2019

(54) METHODS FOR TREATMENT OF M-TOR INHIBITOR-ASSOCIATED STOMATITIS

(71) Applicant: IZUN PHARMACEUTICALS CORP., New York, NY (US)

(72) Inventors: William Z. Levine, Jerusalem (IL); Gabriel Jay Nussbaum, Jerusalem (IL)

(73) Assignee: IZUN PHARMACEUTICALS CORPORATION, New York, NY (US)

( * ) Notice: Subject to any disclaimer, the term of this patent is extended or adjusted under 35 U.S.C. 154(b) by 403 days.

(21) Appl. No.: 15/029,255

(22) PCT Filed: Oct. 14, 2014

(86) PCT No.: PCT/IB2014/065288
§ 371 (c)(1),
(2) Date: Apr. 14, 2016

(87) PCT Pub. No.: WO2015/056160
PCT Pub. Date: Apr. 23, 2015

(65) Prior Publication Data
US 2016/0235798 A1    Aug. 18, 2016

Related U.S. Application Data

(60) Provisional application No. 61/890,344, filed on Oct. 14, 2013.

(51) Int. Cl.
| | | |
|---|---|---|
| *A61K 36/28* | (2006.01) | |
| *A61K 36/185* | (2006.01) | |
| *A61K 36/23* | (2006.01) | |
| *A61K 9/00* | (2006.01) | |
| *A61K 45/06* | (2006.01) | |
| *A61K 47/10* | (2017.01) | |
| *A61K 31/00* | (2006.01) | |

(52) U.S. Cl.
CPC .............. *A61K 36/28* (2013.01); *A61K 9/006* (2013.01); *A61K 31/00* (2013.01); *A61K 36/185* (2013.01); *A61K 36/23* (2013.01); *A61K 45/06* (2013.01); *A61K 47/10* (2013.01)

(58) Field of Classification Search
None
See application file for complete search history.

(56) References Cited

U.S. PATENT DOCUMENTS

| 7,563,466 | B2 * | 7/2009 | Levine | A61K 36/23 |
| | | | | 424/725 |
| 2006/0110482 | A1 * | 5/2006 | Levine | A61K 9/006 |
| | | | | 424/777 |

FOREIGN PATENT DOCUMENTS

| EP | 0533433 A1 * | 3/1993 | ............. A61K 31/70 |
| WO | 02094300 | 11/2002 | |
| WO | 2013136270 | 9/2013 | |

OTHER PUBLICATIONS

Sonis Stephen et al, Preliminary Characterization of Oral Lesions Associated With Inhibitors of Mammalian Target of Rapamycin in Cancer Patients, Cancer Jan. 1, 2010, pp. 210-215, Oct. 27, 2009.
International Search Report dated Feb. 9, 2015 for International Application No. PCT/IB2014/065288 filed Oct. 14, 2014.
European Search Report dated May 19, 2017 issued in corresponding EP Application No. 14854625.2 filed Oct. 14, 2017.
Marcio Augusto De Oliveira et al: "Clinical presentation and management of mTOR inhibitor-associated stomatitis", Oral Oncology, Elsevier Science, Oxford, GB, val. 47, No. 10, Aug. 1, 2011 (Aug. 1, 2011), pp. 998-1003, XP028311692, ISSN: 1368-8375, DOI: 10.1 016/J.Oraloncology.2011.08.009.
Martins Fabiana et al: "A review of oral toxicity associated with mTOR inhibitor therapy in cancer patients", Oral Oncology, val. 49, No. 4, Apr. 2013 (Apr. 2013), pp. 293-298.

\* cited by examiner

*Primary Examiner* — Amy L Clark
(74) *Attorney, Agent, or Firm* — JMB Davis Ben-David

(57) ABSTRACT

Embodiments of the invention relate to a method for the treatment of mIAS or prevention of symptoms associated with mIAS in a patient in need thereof comprising administering to a patient in need thereof an amount of a composition comprising extracts of the plant species *Sambucus nigra*, *Echinacea purpurea*, and *Centella asiatica*. Optionally the ratio of *Sambucus nigra*, *Echinacea purpurea* and *Centella asiatica* is about 7:1:2. Further embodiments relate to use of extracts of the plant species *Sambucus nigra*, *Echinacea purpurea*, and *Centella asiatica* for the manufacture of a medicament for the treatment of mIAS or prevention of symptoms associated with mIAS in a patient in need thereof.

13 Claims, 3 Drawing Sheets

METHODS FOR TREATMENT OF M-TOR INHIBITOR-ASSOCIATED STOMATITIS

RELATED APPLICATIONS

The present application is a US National Phase of PCT Application No. PCT/IB2014/065288, filed on Oct. 14, 2014, which claims the benefit under 35 U.S.C. 119(e) of U.S. Provisional Application 61/890,344 filed on Oct. 14, 2013, the disclosures of which are incorporated herein by reference.

TECHNICAL FIELD

Embodiments of the invention relate to methods for treatment of diseases using herbal extracts and compositions comprising the herbal extracts.

BACKGROUND

Mammalian target of rapamycin, otherwise known as mTOR, is a protein kinase that regulates many cell activities including growth, proliferation and protein transcription. mTOR has been associated with human processes and diseases including aging, transplant rejection and cancer. Many mTOR inhibitors have been identified and/or developed including: rapamycin and analogs thereof, temsirolimus, everolimus, ridaforolimus, sirolimus and deforolimus. Some mTOR inhibitors have been approved for use by health authorities for treatment of various cancers and transplant rejection.

A side effect common in patients receiving mTOR inhibitors is known as mTOR inhibitor-associated stomatitis (mIAS). Incidence of mIAS is estimated at 40-90% of all patients being treated with mTOR inhibitors. Although usually not life-threatening, mIAS occurrence in patients may be painful and may interfere with a patient's routine daily activities such as eating and drinking. Occurrence of mIAS may require reduction of mTOR inhibitor dose or cessation of treatment, thereby limiting the efficacy of the mTOR inhibitor treatment.

SUMMARY

An aspect of an embodiment of the invention relates to methods for prevention or treatment of mIAS in a patient in need thereof comprising administering a composition comprising extracts of the plant species *Sambucus nigra, Echinacea purpurea*, and *Centella asiatica*. According to an embodiment of the invention, the ratio of *Sambucus nigra: Echinacea purpurea:Centella asiatica* is 2-15:0.5-3:0.5-3. According to an embodiment of the invention, the ratio of *Sambucus nigra:Echinacea purpurea:Centella asiatica* is about 7:1:2.

According to an embodiment of the invention, a method is provided comprising: identifying a patient at risk of experiencing mIAS; and administering to the patient a composition comprising extracts of the plant species *Sambucus nigra, Echinacea purpurea*, and *Centella asiatica*, thereby preventing the manifestation of mIAS.

Therapeutic compositions comprising herbal extracts of the plant species *Sambucus nigra, Echinacea purpurea*, and *Centella asiatica* have been described in U.S. Pat. No. 7,563,466 and PCT application publication WO 2013/136270, incorporated by reference.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical structures, elements or parts that appear in more than one figure are generally labeled with a same numeral in all the figures in which they appear. Dimensions of components and features shown in the figures are chosen for convenience and clarity of presentation and are not necessarily shown to scale.

DETAILED DESCRIPTION

Figure 1A:
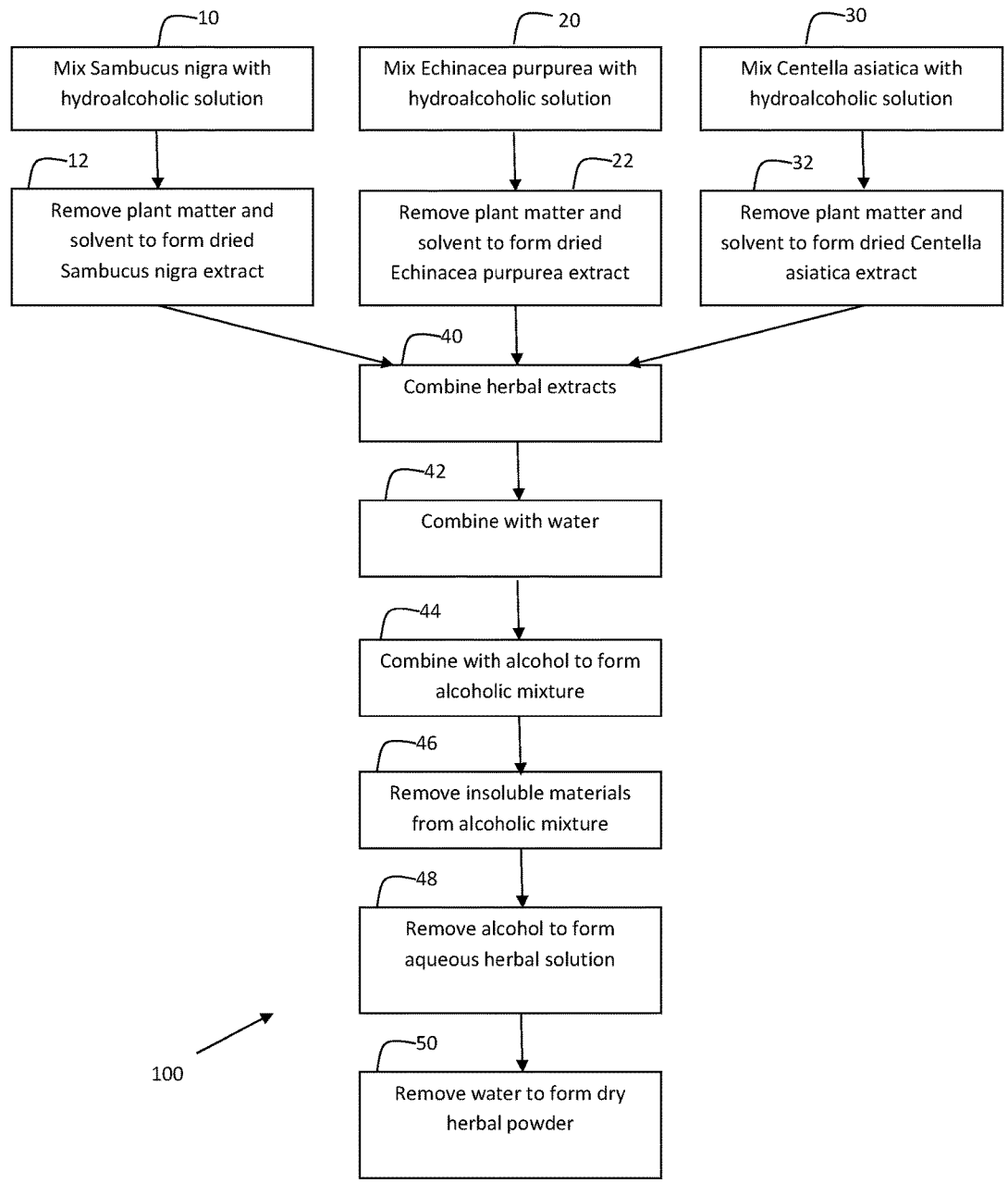
FIGS. 1*a* and 1*b* depict manufacturing process of herbal compositions which may be used according to embodiments of the invention.

Herbal extracts have been associated with treatment of chemical-induced and radiation-induced Oral Mucositis (OM) in PCT Application publication WO 2013/136270. OM is a distinct disease which is different than mIAS. Oral lesions associated with mIAS are discrete, well demarcated ulcers that are present in the movable oral mucosa, but not associated with other gastrointestinal signs. mIAS lesions are typically distinct oval ulcers with a central gray area surrounded by an erythematous band. Lesions associated with mIAS are typically found in the movable oral mucosa and not in the more keratinized mucosa of the palate, gingiva or dorsal surface of the tongue. This distinguishes mIAS lesions from lesions associated with viruses, which may be found in these areas as well (Sonis, 2010).

The inventors have found that herbal extracts comprising *Sambucus nigra, Echinacea purpurea*, and *Centella asiatica* according to embodiments of the invention may be useful in treating and preventing mIAS.

According to an embodiment of the invention, the extracts of the plant species *Sambucus nigra, Echinacea purpurea*, and *Centella asiatica* are administered before appearance of a mIAS lesion. According to an embodiment of the invention, the extracts of the plant species *Sambucus nigra, Echinacea purpurea*, and *Centella asiatica* are administered after appearance of a mIAS lesion.

In the detailed description below, aspects of embodiments of the invention are discussed with respect to methods of treatment of mIAS and pharmaceutical compositions for treating mIAS comprising *Sambucus nigra, Echinacea purpurea*, and *Centella asiatica*.

In additional embodiments of the invention, the composition of the present invention further comprises an extract of the plant species *Hypericum perforatum* and *Commiphora molmol, Uncaria tomentosa, Thymus vulgaris, Matricaria recutita, Salix alba, Calendula officinalis, Usnea barbata, Ligusticum porterii-osha, Gaultheria procumbens, Camellia sinensis, Vaccinium myrtilltus, Melissa officinalis, Allium sativum, Camellia sinensis, Hamamelis virginiana* or *Krameria triandra*.

In additional embodiments of the invention, the composition of the present invention further comprises an additional mIAS-treating agent. The agent may be selected from the group consisting of a steroid and hyaluronic acid.

In additional embodiments of the invention, pharmaceutical compositions may be prepared in the form of patches, ointments, pastes, lotions, creams, lozenges, candies, chewing gums, solutions, gels, foams and sprays. Pharmaceutical compositions may be prepared, according to embodiments of the invention, in the form of immediate release or delayed release compositions. In a preferred embodiment of the invention, a pharmaceutical composition in the form of an oral rinse may be administered to a subject in need thereof.

Embodiments of the invention provide methods for treatment comprising administering a composition comprising between 1 mg and 1.5 g of active ingredients per day. In an embodiment of the invention, the daily dosage is about 625 mg/day. In an embodiment of the invention, the daily dosage is about 450 mg/day. In another embodiment of the invention, the daily dosage is about 900 mg/day.

According to embodiments of the invention in which an oral rinse is administered as a pharmaceutical composition, the dosage amount is administered to a patient and subsequently expectorated, preferably after circulating in mouth for 15-120 seconds.

According to an embodiment of the invention, an mTOR inhibitor is administered to a patient in combination with a pharmaceutical compositions comprising *Sambucus nigra, Echinacea purpurea*, and *Centella asiatica*.

"In combination" refers to both drugs being substantially effective in the body at a same time. Both drugs can be administered substantially at the same time, or both drugs can be administered at different times but have effect on the body at the same time. For example, "in combination" includes administering a pharmaceutical composition comprising *Sambucus nigra, Echinacea purpurea*, and *Centella asiatica* before the administration of the mTOR inhibitor, and subsequently administering mTOR inhibitor while functioning of the pharmaceutical composition comprising *Sambucus nigra, Echinacea purpurea*, and *Centella asiatica* in the body is substantially extant. Also included is administering an mTOR inhibitor before the administration of pharmaceutical composition comprising *Sambucus nigra, Echinacea purpurea*, and *Centella asiatica*, and subsequently administering the pharmaceutical composition comprising *Sambucus nigra, Echinacea purpurea*, and *Centella asiatica* while the mTOR inhibitor in the body is substantially extant. "In combination" may be in a single dosage form, or in two, or more separate dosage forms, administered simultaneously or separately.

Without being bound by theory, it is suggested that a mechanism of action which may be present upon use of the pharmaceutical composition comprising *Sambucus nigra, Echinacea purpurea*, and *Centella asiatica* in a patient, relates to induction of tissue inhibitors of matrix metalloproteinases, as shown in greater detail in the examples below.

Methods for manufacturing herbal extracts, methods for treatment using the herbal extracts and mechanistic models using herbal extracts are described in detail in the following, non-limiting examples.

EXAMPLE 1a

Synthesis of Herbal Extracts, General Scheme

FIG. 1a shows a flow-diagram depicting a synthetic scheme 100 for synthesizing various compositions comprising extracts from the plant species *Sambucus nigra, Echinacea purpurea*, and *Centella asiatica*. Synthetic scheme 100 comprises blocks 10, 20, and 30 comprising mixing *Sambucus nigra, Echinacea purpurea* and *Centella asiatica* respectively with a hydroalcoholic solution (a solution comprising water and an alcohol). Blocks 12, 22 and 32 comprise removing insoluble plant matter and solvent to form dried extracts of *Sambucus nigra, Echinacea purpurea* and *Centella asiatica* respectively. Block 40 comprises combining dried herbal extracts of block 12, 22 and 32.

In an embodiment of the invention, the hydroalcoholic solution of block 10, 20 and/or 30 comprises between 25 and 75% alcohol. In an embodiment of the invention, the hydroalcoholic solution of block 10, 20 and/or 30 comprises 70% alcohol. In an embodiment of the invention, the alcohol in the hydroalcoholic solution comprises ethanol. In an embodiment of the invention, the ratio of solvent to plant in block 10, 20 and/or 30 is between about 6 to about 10 parts by weight of solvent to one part by weight of plant material. In an embodiment of the invention, the ratio of solvent to plant in block 10, 20 and/or 30 is between about 8:1 by weight. In an embodiment of the invention, the hydroalcoholic solution is mixed with plant material for about 8 hours. In an embodiment of the invention, the extraction process is multi-stage. In an embodiment of the invention, the hydroalcoholic solution is mixed at a temperature of about 30-40 degrees C. (Celsius.) In an embodiment of the invention, an excipient is added to the hydroalcoholic solution before removal of solvent and plant matter. In an embodiment of the invention, the excipient is a carrier, for example, maltodextrin. In an embodiment of the invention the excipient is colloidal anhydrous silica. In an embodiment of the invention, the ratio of herbal extract to excipient is about 7:3.

In an embodiment of the invention, solvent is removed in block 12, 22 and/or 32 by spray drying.

In an embodiment of the invention, in block 40, herbal extracts of *Sambucus nigra, Echinacea purpurea* and *Centella asiatica* are combined in a weight ratio of 2-15:0.5-3:0.5-3 respectively. In another embodiment, herbal extracts of *Sambucus nigra:Echinacea purpurea:Centella asiatica* are combined in a weight ratio of 70:10:20 respectively.

Synthetic scheme 100 further comprises block 42, comprising combining water with the combined herbal extract of block 40. In an embodiment of the invention, water is combined in a ratio of 3 to 14 liters (L) of water for every kilogram (kg) of herbal extract. In an embodiment of the invention, water is combined in a ratio of 9 L of water for every kg of herbal extract. In an embodiment of the invention, the water and herbal extract mixture is mixed for about 6 to about 24 hours. In an embodiment of the invention the water and herbal extract mixture are mixed for about 12 hours.

Synthetic scheme 100 further comprises block 44, comprising combining alcohol with the mixture formed in block 42. In an embodiment of the invention the alcohol comprises ethanol. In an embodiment of the invention, 96% or 100% ethanol is used to form an alcoholic mixture having a concentration of about 50% to about 90% ethanol. In an embodiment of the invention, the ethanol is added to reach a concentration of 70% ethanol.

In an embodiment of the invention, the alcoholic mixture of block 44 is stirred for about 6 to about 24 hours, preferably for about 12 hours.

Synthetic scheme 100 further comprises block 46, comprising removing insoluble materials from the alcoholic mixture formed in block 44. In an embodiment of the invention, the insoluble materials are removed from the alcoholic mixture using centrifugation, filtration, settling or a combination of any of these methods.

Synthetic scheme 100 further comprises block 48, comprising removal of alcohol to form an aqueous herbal solution. In an embodiment of the invention, alcohol can be removed by distillation or by evaporation using a rotary evaporator. In an embodiment of the invention, the alcohol is ethanol and is removed using a rotary evaporator at a temperature of less than 30 degrees C.

Synthetic scheme 100 further comprises block 50, comprising removal of water from the aqueous solution of block 48 to form a dry herbal powder. Removal of water may be accomplished, according to embodiments of the invention, using lyophilization (freeze drying) or spray drying.

Figure 1B:
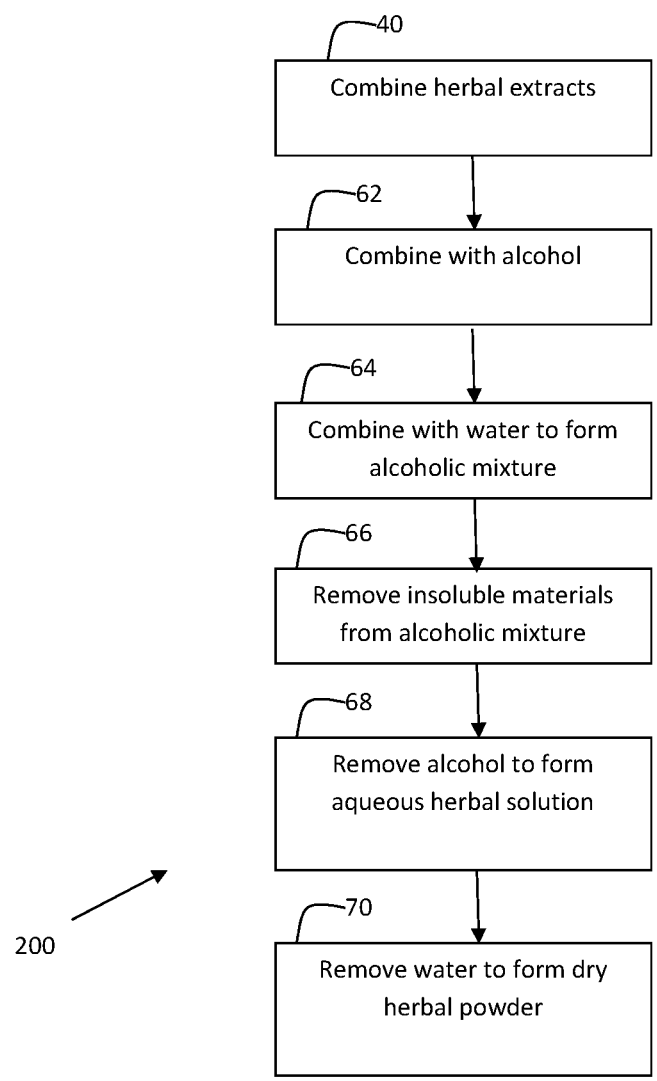

FIG. 1b shows a flow-diagram depicting synthetic scheme 200 for synthesizing various compositions comprising extracts from the plant species *Sambucus nigra*, *Echinacea purpurea*, and *Centella asiatica*. Synthetic scheme 200 comprises block 40, comprising combining dried herbal extracts of block 12, 22 and 32 in synthetic scheme 100 as described.

In an embodiment of the invention, in block 40, herbal extracts of *Sambucus nigra:Echinacea purpurea:Centella asiatica* are combined in a weight ratio of 2-15:0.5-3:0.5-3 respectively. In another embodiment of the invention, herbal extracts of *Sambucus nigra, Echinacea purpurea:Centella asiatica* are combined in a weight ratio of 70:10:20 respectively.

Synthetic scheme 200 further comprises block 62, comprising combining alcohol with the combined herbal extract of block 40. In an embodiment of the invention, alcohol is used in a ratio of about 3 to about 14 L alcohol, preferably about 9 L of alcohol for every kg of herbal extract. In an embodiment of the invention, the alcohol and herbal extract mixture is mixed for about 12 hours. In an embodiment of the invention the alcohol comprises ethanol. In an embodiment of the invention, the ethanol is 96%-100% ethanol.

Synthetic scheme 200 further comprises block 64, comprising combining water with the mixture formed in block 62. In an embodiment of the invention, water is used to form an alcoholic mixture having a concentration of about 50% to about 90% ethanol. In an embodiment, the water is used to reach a concentration of 70% ethanol.

In an embodiment of the invention, the alcoholic mixture of block 64 is stirred. In an embodiment of the invention, the mixture is stirred for about 6 hours to about 24 hours, preferably for about 12 hours.

Synthetic scheme 200 further comprises block 66, comprising removing insoluble materials from the alcoholic mixture formed in block 64. In an embodiment of the invention, the insoluble materials are removed from the alcoholic mixture using centrifugation, filtration, settling, or any combination of these methods.

Synthetic scheme 200 further comprises block 68, comprising removal of alcohol to form an aqueous herbal solution. In an embodiment of the invention, alcohol can be removed using distillation or evaporation, for example, using a rotary evaporator. In an embodiment of the invention, the alcohol is ethanol and is removed using a rotary evaporator at a temperature of less than 30 degrees C.

Synthetic scheme 200 further comprises block 70, comprising removal of water from the aqueous solution of block 68 to form a dry herbal powder. Removal of water may be accomplished, according to embodiments of the invention, using lyophilization (freeze drying) or spray drying.

EXAMPLE 1b

Synthesis of Herbal Extract N

Synthetic scheme 100 described in example 1a was followed with the following details, in accordance with an embodiment of the invention.

*Sambucus nigra* (flowering tops) was mixed with 70% ethanol (8:1 solvent to plant ratio) according to block 10. Upon removing insoluble plant matter and drying solvent according to block 12, 3.29 kg of dried *Sambucus nigra* extract were formed.

*Echinacea purpurea* (rhizome and roots) was mixed with 70% ethanol (8:1 solvent to plant ratio) according to block 20. Upon removing insoluble plant matter and drying solvent according to block 22, 470 g (grams) of dried *Echinacea purpurea* extract were formed.

*Centella asiatica* (aerial parts) was contacted with 70% ethanol (8:1 solvent to plant ratio) according to block 30. Upon removing insoluble plant matter and drying solvent according to block 32, 940 g of dried *Centella asiatica* extract were formed.

The three dried extracts from the three herbs (ratio of 70:10:20 by weight) were combined in accordance with block 40. In accordance with block 42, 47 L of water were added and the mixture was stirred for 12 hours. 113.9 L of 96% ethanol was added to the mixture to form 160.9 L of a 70% ethanol alcoholic mixture according to block 44. The mixture was filtered in accordance with block 46 and the insoluble material was removed. Ethanol was evaporated in accordance with block 48 and the solution was spray-dried according to block 50 to form 3.2 kg of a dry herbal powder, designated as Extract N. The yield of this process (percentage by weight relative to dried extracts added according to block 40) was 68.7%.

EXAMPLE 1c

Preparation of Mouth Rinse 2.601 kg of Extract N was stirred for 12 hours with 10.379 kg of propylene glycol (PG) and 26.01 g sucralose to form a concentrate solution. 2.5 g of concentrate solution was mixed with 47.5 ml of saline solution to prepare a mouth rinse.

EXAMPLE 2a

Tissue Inhibitor of Metalloproteinase (TIMPs) Induction Using Herbal Extracts

The matrix metalloproteinases (MMPs) are enzymes that play a key role in the normal physiology of connective tissue during development, morphogenesis and wound healing, but their unregulated activity has been implicated in numerous disease processes including epithelial ulcerative processes, arthritis, tumor cell metastasis and atherosclerosis. TIMPs regulate the activities of MMPs, and an imbalance between MMPs and TIMPs results in pathological tissue destruction that leads to ulceration.

TIMPs are small (22-30 kDa), naturally occurring proteins capable of binding and inactivating MMPs. Four TIMPs have been identified (TIMP-1, TIMP-2, TIMP-3, and TIMP-4), each with its own physiologic role. The common thread within this family of enzymes is their ability to form non-covalent bonds with latent and active forms of MMPs. TIMP-3 has multiple targets and acts through multiple pathways as shown by the varied polymorphisms in the TIMP-3 gene associated with disease. TIMP-3 is produced by many cell types, and it is found in both saliva and gingival crevicular fluid (GCF). TIMP-3 is a broad spectrum inhibitor of MMPs, having been shown to inhibit many MMPs. The levels of TIMPs in healthy oral tissue are high and have been shown to decrease in inflammatory disease states. The constitutive expression and evolutionary conservation of TIMP-3 imply its important function. TIMP-3 is induced by transforming growth factor beta (TGF-β) an important factor in mucosal tissue protection and wound healing, further supporting the importance of TIMP-3 in mucosal protection and health. Induction of TIMP-3 by herbal extracts represents a mechanism through which the extracts may protect the mucosa from agents known to induce ulceration. Without being bound by theory, it is suggested that increased levels of TIMP-3 in patients susceptible to mIAS, such as patients who are receiving m-TOR inhibitors, may prevent, delay the onset and/or reduce the severity of mIAS.

To confirm induction of TIMP-3 by the botanical extracts, fibroblasts were incubated with herbal extract *Sambucus nigra*, *Centella asiatica*, and *Echinacea purpurea* as prepared in accordance with example 1a at different concentrations, or with TGF-β as a positive control. The induced protein was visualized using a reverse zymogram technique.

Reverse zymography is a widely used assay to analyze the activity of TIMPs. Reverse zymography involves the electrophoretic separation of proteins under denaturing (sodium dodecyl sulfate, SDS) but non-reducing conditions through a poly-acrylamide gel containing gelatin, and inactive MMP-2 (gelatinase). Once the proteins are separated on the gel, the MMP-2 is activated using buffers and the gelatin is stained with a blue dye. Since the entire gel contains both gelatin (stained with a blue dye) and MMP-2, the degradation of gelatin is observed as a clearing of the blue color of the gel. Since the TIMP inhibits MMP-2 activity, there will be a blue band present at the molecular weight of the TIMP protein if it is present in the sample.

TIMP-3 activity was assayed using reverse zymography with a reverse zymography kit developed by Dylan Edwards, Ph.D., University of East Anglia, UK. HGF-1 (human gingival fibroblast) and HLF (human lung fibroblast) cell lines, all obtained from the American Type Culture Collection (ATCC, Manassas, Va., USA), were used in this assay. Cell lines were grown in cell culture medium (Dulbecco's modified Eagle's medium, DMEM, supplemented with 10% heat-inactivated fetal bovine serum, 2 or 4 millimolar glutamine, and 1 millimolar sodium pyruvate.) HLF was seeded at a density of $2.5 \times 10^5$ cells/well; HGF-1 was seeded at a density of $2.0 \times 10^5$ cells/well. Two ml of cell culture were deposited per well in 6 well plates and cells allowed to adhere and grow at 37° C., 5% $CO_2$, for 24 hours. Growth medium was replaced with starvation medium (DMEM 4 mM glutamine, 1 mM sodium pyruvate, 100 IU/mL penicillin, 0.1 mg/mL streptomycin, and 0.1% BSA) with or without transforming growth factor-beta (TGF-β; R&D Systems, Minneapolis, Minn., USA) or herbal extract, at a concentration of either 0.75 mg/ml or 1.5 mg/ml for an additional 24 hours. Conditioned medium was removed from each well, vacuum-dried to concentrate, and re-suspended in 400 μl of 0.1% SDS. Depending on the size of the well, 10-15 μl of the sample was loaded in the gel after being mixed at a 1:3 ratio of buffer to sample. The gel was then run at 200V for about 3 hours or until the purple bands of the dye have progressed about three quarters of the way down the gel. The gels were then washed in rinse buffer (50 mM Tris, 5 mM $CaCl_2$ and 25 g Triton-X 100) for 2.5 hours, followed by incubation buffer (rinse buffer without Triton-X 100) at 37° C. overnight. The gels were stained in Coomassie Blue (Bio-Rad, Hercules, Calif., USA) for 2.5 hours and destained until a bright blue band was obtained against a clear background. The image was captured with a CCD camera (DNR Bio-Imaging Systems, Jerusalem, Israel). Densitometry was performed with TotalLab software (Non-linear Dynamics, Newcastle-Upon-Tyne, UK).

Figure 2:
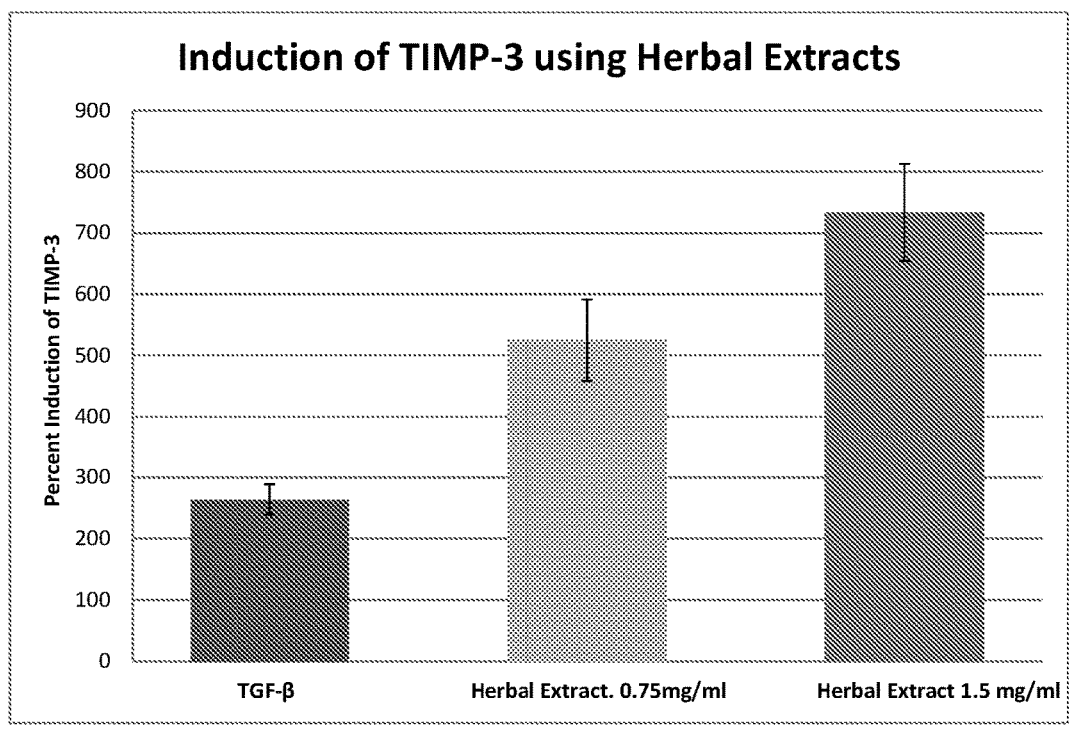
FIG. 2 shows a bar graph depicting relative induction of tissue inhibitor of metalloproteinase-3 (TIMP-3) in cells exposed to herbal extracts and in cells exposed to TGF-β positive control.

The results of TIMP-3 induction in cells treated with TGF-β and two doses of herbal extract were compared to induction of sample cells which received growth medium alone (without TGF-β and without herbal extract) to calculate relative percentage of of TIMP-3 induction. The results are shown in FIG. 2.

The treatment of fibroblasts with the plant extracts induced production of active TIMP-3, up to 2-3 times the level of TIMP-3 produced when fibroblasts were treated with the positive control, TGF-β. This indicates that the herbal extracts may be useful in treatment and prevention of mIAS in patients in need thereof.

EXAMPLE 2b

Use of Herbal Extracts in an Animal Model of mIAS

Male Syrian Golden Hamsters ("hamsters") weighing approximately 95 g are administered 0.125 mg per kg of bodyweight of everolimus or other equivalent mTOR inhibitor, until appearance of mIAS-like oral symptoms such as apthous ulcers. Upon appearance of symptoms, hamsters are split into two groups, each group having a similar symptomatic profile. The two hamster groups are a vehicle control group of eight hamsters and a treatment group of eight hamsters. Hamsters are administered to the oral cavity either vehicle alone, consisting of 0.2 ml of solvent (vehicle control group) or a preparation comprising 1% extract N in 0.2 ml of solvent (treatment group). Solvents may be full strength water, various proportions of propylene glycol in water, or other materials.

Preparations (for vehicle control group and for active treatment group) are administered topically three times daily for 21 days Hamster condition is assessed daily and body weights are measured once daily by technicians blinded to the identity of each hamster group. The duration and severity of mIAS-like symptoms on each day of measurement are compared between the treatment group and the untreated control group to determine the impact of the treatment on the course of mIAS-like symptoms. It is suggested that by the end of the study, hamsters receiving active treatment according to embodiments of the invention may show fewer mIAS-like symptoms than hamsters in the vehicle control group.

EXAMPLE 2c

Use of Herbal Extracts in an Additional Animal Model of mIAS

A model is performed as in example 2b, with variation of initiating treatment of both hamster groups upon initiation of everolimus treatment, before appearance of mIAS-like oral symptoms.

It is suggested that hamsters receiving treatment with compositions according to embodiments of the invention may show a delay and/or a prevention of mIAS like symptoms compared to hamsters in the vehicle control group.

EXAMPLE 3a

Testing in Humans

A double blind, randomized, placebo controlled, fixed-dose, comparative study testing effects of mouth rinse according to example 1c in mIAS is performed in patients undergoing mTOR inhibitor treatment for cancer. Patients are randomized to receive either active mouth rinse or a placebo according to a 1:1 randomization schedule. Rinse dose is 15 ml of 1% oral rinse, as described in example 1c, at a frequency of three times daily. The placebo is prepared using propylene glycol, sucralose and food coloring, diluted in saline.

About 100 subjects receive treatment with the test articles for approximately 21 days along with mTOR treatment, starting on the day that the subjects begin mTOR treatment. Treatment may be continued for a month after mTOR treatment and/or through a second 21 days cycle of mTOR treatment.

Safety is evaluated by general toxicity based on vital signs and physical examinations. Efficacy is evaluated by comparing incidence of mIAS, severity scores, need for lowering of mTOR inhibitor dose in patients, dose interruptions due to mIAS symptoms in patients receiving placebo versus patients receiving active oral rinse. Efficacy can be measured by rating patients according to the following scale: Grade 0: No mIAS or mucosal lesions. Grade 1: erythema, mucosal sensitivity and pain. Grade 2: Ulceration, ability to eat solid foods. Grade 3: Ulceration, oral intake limited to fluids. Grade 4: Ulceration, oral feeding is impossible.

It is suggested that active oral rinse according to embodiments of the invention is effective in prevention of occurrence of symptoms of mIAS and/or treatment of mIAS symptoms, relative to placebo.

EXAMPLE 3b

Further Testing in Humans

An open label study is performed in patients undergoing mTOR inhibitor treatment for cancer. Patients are randomized to receive either active mouth rinse (as described in example 3a,) or standard of care mIAS treatment consisting of topical high potency corticosteroids, topical nonsteroidal anti-inflammatory drugs (amiexanox 5% oral paste) and/or topical anesthetic (viscous lidocaine 2%.) Patients are administered with treatments upon appearance of mIAS type symptoms.

Safety is evaluated by general toxicity based on vital signs and physical examinations. Efficacy is evaluated by comparing incidence of mIAS, severity scores, need for lowering of mTOR inhibitor dose in patients, dose interruptions due to mIAS symptoms in patients receiving standard of care versus patients receiving active oral rinse.

It is suggested that oral rinse according to embodiments of the invention is effective in treating mIAS relative to standard of care. In addition, oral rinse according to embodiments of the invention does not have negative side effects typically associated with corticosteroids such as oral candidiasis (thrush) and other potential side effects.

There is further provided in accordance with an embodiment of the invention a method for the treatment of mIAS or prevention of symptoms associated with mIAS in a patient in need thereof comprising administering to a patient in need thereof an amount of a composition comprising extracts of the plant species *Sambucus nigra*, *Echinacea purpurea*, and *Centella asiatica*. Optionally, the ratio of *Sambucus nigra*, *Echinacea purpurea* and *Centella asiatica* is about 7:1:2. Optionally, the patient is receiving an mTOR inhibitor treatment. Optionally, the patient is receiving an mTOR inhibitor treatment for cancer or organ transplantation. Optionally, the composition is in the form of an oral rinse. Optionally the composition is in the form of an oral patch. Optionally, the composition is administered to the patient before appearance of mIAS symptoms. Optionally the composition is administered to the patient after appearance of a mIAS symptom. Optionally, the mTOR inhibitor and the composition are administered in combination. Optionally, the composition is administered in an amount of 1 mg and 1.5 g of extract per day. Optionally, the composition is administered in an amount of 625 mg of extract per day. Optionally, the composition is administered in an amount of 450 mg of extract per day. Optionally, the composition is administered in an amount of 900 mg of extract per day. Optionally, the composition is administered in an amount in which TIMP-3 levels are increased in the patient. Optionally, the composition further comprises at least one pharmaceutically acceptable excipient. Optionally, the composition further comprises propylene glycol. Optionally, the weight ratio between the plant extract and propylene glycol is about 1 to 4. Optionally, the mTOR inhibitor is selected from the group consisting of: rapamycin, rapamycin analogs, temsirolimus, everolimus, ridaforolimus, sirolimus and deforolimus. Optionally, the composition comprises about 0.5% to about 2% plant extract. Optionally, the composition comprises about 1% plant extract. Optionally, the compositions further comprises one or more additional extracts derived from a plant selected from the group consisting of: *Hypericum perforatum*, *Commiphora molmol*, *Uncaria tomentosa*, *Thymus vulgaris*, *Matricaria recutita*, *Salix alba*, *Calendula officinalis*, *Usnea barbata*, *Ligusticum porterii-osha*, *Gaultheria procumbens*, *Camellia sinensis*, *Vaccinium myrtilltus*, *Melissa officinalis*, *Allium sativum*, *Camellia sinensis*, *Hamamelis virginiana* and *Krameria triandra*.

There is further provided in accordance with an embodiment of the invention a pharmaceutical composition for the treatment of mIAS or prevention of symptoms associated with mIAS in a patient in need thereof comprising extracts of the plant species *Sambucus nigra*, *Echinacea purpurea*, and *Centella asiatica*.

There is further provided in accordance with an embodiment of the invention a use of extracts of the plant species *Sambucus nigra*, *Echinacea purpurea*, and *Centella asiatica* for the manufacture of a medicament for the treatment of mIAS or prevention of symptoms associated with mIAS in a patient in need thereof.

In the description and claims of the present application, each of the verbs, "comprise," "include" and "have," and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

WORKS CITED

Sonis, S. e. (2010). Preliminary Characterization of Oral Lesions Associated with Inhibitors of Mammalian Target of Rapamycin in Cancer Patients. Cancer, 210-215.

The invention claimed is:

1. A method for treating mammalian target of rapamycin (mTOR) inhibitor associated stomatitis (mIAS) in a patient in need thereof, comprising administering an effective amount of a composition comprising *Sambucus nigra, Echinacea purpurea*, and *Centella asiatica* extracts to said patient.

2. The method according to claim 1, wherein the ratio of *Sambucus nigra, Echinacea purpurea* and *Centella asiatica* is about 7:1:2.

3. The method according to claim 1, wherein the patient is receiving an mTOR inhibitor treatment.

4. The method according to claim 3, wherein the patient is receiving an mTOR inhibitor treatment for cancer or organ transplantation.

5. The method according to claim 1, wherein the composition is in the form of an oral rinse.

6. The method according to claim 1, wherein the composition is in the form of an oral patch.

7. The method according to claim 1, wherein the composition is administered to the patient after an mIAS symptom appears.

8. The method according to claim 3, wherein the composition is administered in combination with an mTOR inhibitor.

9. The method according to claim 1, wherein the amount of the composition is effective to increase TIMP-3 levels in the patient.

10. The method according to claim 1, wherein the composition further comprises at least one pharmaceutically acceptable excipient.

11. The method according to claim 5, wherein the composition further comprises propylene glycol.

12. The method according to claim 11, wherein the weight ratio of the extracts and propylene glycol is about 1 to 4.

13. The method according to claim 8, wherein the mTOR inhibitor is selected from the group consisting of: rapamycin, rapamycin analogs, temsirolimus, everolimus, ridaforolimus, sirolimus and deforolimus.

* * * * *